(12) United States Patent
Renier et al.

(10) Patent No.: US 9,687,558 B2
(45) Date of Patent: Jun. 27, 2017

(54) ANTITUMORAL BIOCONJUGATES OF HYALURONIC ACID OR ITS DERIVATIVES OBTAINED BY INDIRECT CHEMICAL CONJUGATION, AND THEIR USE IN THE PHARMACEUTICAL FIELD

(75) Inventors: Davide Renier, Abano Terme-Padua (IT); Fabio Bettella, Abano Terme-Padua (IT)

(73) Assignee: FIDIA FARMACEUTICI S.P.A., Abano Terme-Padova (IT)

( * ) Notice: Subject to any disclaimer, the term of this patent is extended or adjusted under 35 U.S.C. 154(b) by 962 days.

(21) Appl. No.: 11/989,716

(22) PCT Filed: Aug. 2, 2006

(86) PCT No.: PCT/EP2006/007717
§ 371 (c)(1),
(2), (4) Date: Mar. 4, 2008

(87) PCT Pub. No.: WO2007/014784
PCT Pub. Date: Feb. 8, 2007

(65) Prior Publication Data
US 2008/0292703 A1    Nov. 27, 2008

(30) Foreign Application Priority Data
Aug. 3, 2005 (IT) .............................. PD2005A0242

(51) Int. Cl.
A61K 47/48    (2006.01)

(52) U.S. Cl.
CPC ................................ A61K 47/4823 (2013.01)

(58) Field of Classification Search
None
See application file for complete search history.

(56) References Cited

U.S. PATENT DOCUMENTS

| 5,648,506 A | 7/1997 | Desai et al. |
| 5,874,417 A * | 2/1999 | Prestwich et al. ............... 514/54 |
| 2006/0116346 A1 | 6/2006 | DeLuca et al. |

FOREIGN PATENT DOCUMENTS

| WO | WO 02/087498 A2 | 11/2002 |
| WO | WO 02/090390 A | 11/2002 |
| WO | WO 2004/035629 | * 4/2004 |

OTHER PUBLICATIONS

Okuno, S. et al "Complete regression of xenografted carcinoma . . . " Cancer Res. (2000) vol. 60, pp. 2988-2995.*
Reijnen, M. et al "Prevention of intra-abdominal abscesses and adhesions . . . " Arch. Surg. (1999) vol. 134, pp. 997-1001.*
Exner, A. et al "Enhancement of carboplatin toxicity by pluronic block copolymers" J. Controlled Release (2005) vol. 106, 188-197.*
Maeda, H. et al "Conjugates of anticancer agents and polymers . . . " Bioconj. Chem. (1992) vol. 3, No. 5, pp. 351-362.*
De Stefano, I. et al "Hyaluronic acid-paclitaxel: effects of intraperitoneal . . . " Cancer Chemother. Pharmacol. (2011) vol. 68, pp. 107-116.*
Tringali, G. et al "The in vitro rabbit whole bladder as a model . . . " Pharmacol. Res. (2008) vol. 58, pp. 340-343.*
International Search Report, Mar. 23, 2007.
Sparer R V et al., Controlled Release Delivery Systems pp. 107-119 (1983).
Li H. et al, Synthesis and Biological Evaluation of a Cross-linked Hyaluronan-Mitomucin C hydrogel Biomacromolecules, (5) pp. 895-902 (2004).
Akima K et al., Activities of Hyaluronate Binding Anti-Tumor Drugs, J. Drug Targeting (4) No. 1 pp. 1-8 (1996).
Lou, Y. et al., "A Hyaluronic Acid-Taxol Antitumor Bioconjugate Targeted to Cancer Cell", Biomacromolecules, vol. 1, pp. 208-218, 2000.
Rosato, A, et al "HYTAD1-p20: A new paclitaxel-hyaluronic acid hydrosoluble bioconjugate for treatment of superficial bladder cancer", Urologic Oncology, vol. 24, pp. 207-215, 2006.

(Continued)

*Primary Examiner* — Leigh C Maier
(74) *Attorney, Agent, or Firm* — Birch, Stewart, Kolasch & Birch, LLP (57) ABSTRACT

The present invention describes a new group of bioconjugates which can be obtained by means of indirect synthesis, via a molecular spacer, between hyaluronic acid and/or its derivatives and drugs with an antitumoral activity belonging to different groups, their preparation process and use in the oncological field. The new derivatives, in relation to the type of bond and Substitution degree, have different physico-chemical properties which improve their tolerability and efficiency and allow a more accurate modulation of the dosage, exploiting an active targeting mechanism.

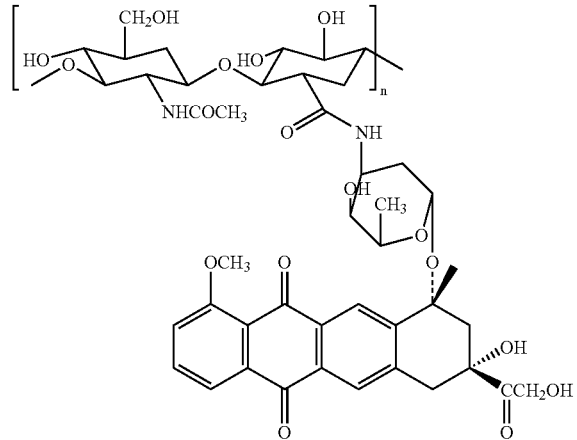

14 Claims, 4 Drawing Sheets

(56) References Cited

OTHER PUBLICATIONS

Luo, Y. et al., "Synthesis and Selective Cytotoxicity of a Hyaluronic Acid-Antitumor Bioconjugate", Bioconjugate Chem., vol. 10, pp. 755-763, 1999.

Luo, Y. et al., "Targeted Delivery of Doxorubicin by HPMA Copolymer-Hyaluronan Bioconjugates", Pharmaceutical Research, vol. 19, No. 4, pp. 369-402, 2002.

\* cited by examiner

ANTITUMORAL BIOCONJUGATES OF HYALURONIC ACID OR ITS DERIVATIVES OBTAINED BY INDIRECT CHEMICAL CONJUGATION, AND THEIR USE IN THE PHARMACEUTICAL FIELD

This Application is the National Phase Under 35 U.S.C. §371 of PCT International Application No. PCT/EP2006/007717, which has an International filing date of Aug. 2, 2006, which claims priority to Italy Patent Application PD2005A000242, filed on Aug. 3, 2005. The entire contents of all applications listed above are hereby incorporated by reference.

The development of a tumor, its growth and progression towards primary and secondary metastases are highly complex biological processes which require a sequential organization of cellular events (organo-selective) coordinated with each other.

The dissemination of tumoral cells which leads to the formation of a metastasis occurs as a result of their detachment from the primary growth site followed by their penetration into the circulatory bed and/or into the lymphatic system.

In the last few years, the progressive knowledge of vital processes which cause the start, development, dissemination and implantation of a tumor and its metastasis, has not only offered researchers the possibility of studying, synthesizing and/or experimenting new chemical molecules as new antitumoral agents but has also facilitated the study and perfecting of new treatment therapies which overcome problems linked to the toxicity of antineoplastic drugs and, above all, an understanding of the chemical-biological mechanisms which cause resistance to the above drug.

One of the main problems linked to the treatment of tumors does in fact relate to the possible "resistance" of the tumor to pharmacological treatment after an initial positive response.

These "resistances" are associated with biological/biochemical variations in the functioning of the tumoral cell such as, for example:
alterations in the cellular transportation of the drug;
affinity changes with respect to this on the part of a possible metabolic inhibitor;
substantial increase in the capacity of the cell itself of inactivating the drug.

Recently published scientific experimentations (Misra et al., The Journal of Biological Chemistry, 2003, 278(28): 25285-25288) have demonstrated how the pre/co-treatment in vitro of tumoral cells resistant to some chemotherapy drugs with oligomers of hyaluronic acid having a very low molecular weight, re-established the initial sensitivity of the cell to the drug. The experimental data so far obtained, however, have not completely clarified how/why the sensitivity to chemotherapy is re-established, even if it has been observed that these oligomers are able to interfere with various molecular events inside the cell responsible for the acquisition of resistance to the drug and therefore of the growth and diffusion of the tumor.

The pharmacological action of the above oligomer becomes possible because, as it binds itself to the CD-44 receptor (specifically of hyaluronic acid), it manages to negatively interfere with the HA native-receptor bond, an interaction which is responsible for the coordination of numerous cell functions and, above all, of the tumoral cell.

Through its binding (and subsequent internalisation) with its receptor present in the cellular membrane, the HA does in fact participate in the activation of many events which are of fundamental importance for the cell life such as, for example, the regulation of the adhesion/growth processes and cellular migration, it enters the chemotactic mechanism during inflammatory processes, plays a main role in cicatrisation processes and, as mentioned above, in the migration of tumoral cells for the formation of metastases.

Many solid tumors have in fact shown high quantities of HA which can consequently facilitate the invasion of other tissues and organs on the part of tumoral cells.

Tumoral forms such as, for example, carcinomas, melanomas, lymphomas, breast tumors, colon-rectal and lung tumors, over-express the transmembrane receptor CD-44: in these cellular lines, experimentations effected with anti-receptor antibodies (which consequently "block" the receptor preventing its binding to the native HA) have shown the effective capacity of inhibiting growth and the tumoral metastases, this demonstrating how the "interference" of the HA bond with its receptor causes a disturbance of numerous events of fundamental importance for the cell life and showing, consequently, the actual participation of the HA in the development of the tumoral mass.

It is known that some antitumoral drugs which have been used for years in the oncological field with satisfactory clinical results have been chemically modified to:
overcome the problem of their intrinsic toxicity with the aim of effecting a new treatment strategy consisting of guiding the antineoplastic drug directly to the tumoral cell binding it to the HA in that, as fully described above, many tumoral phenotypes over-express the specific CD-44 receptor for HA on their cellular surface (this is an active targeting mechanism which increases the cellular efficacy of the drug by reducing its systemic toxicity). The binding and internalisation of the polymer also carry the drug inside the tumoral cell increasing its efficacy;
increase their solubility (it has been demonstrated that the binding of liposoluble drugs with strongly hydrophilic molecules such as, for example, HA, considerably increases the solubility of the drug itself in the circulatory system).

The solubility of chemotherapy drugs in the circulatory bed does in fact represent the essential condition for their pharmacological efficacy, some drugs, however, which have proved to be extremely active in various types of tumors such as, for example, camptothecins and their irinotecan and topotecan derivatives, paclitaxel and alkaloids, Vinca derivatives, as a result of their high insolubility have problems relating to intravenous administration (and, for hormones and anti-hormones also intramuscular) which can limit and restrict their clinical application.

For the reasons cited above (solubility and toxicity) new chemotherapy drugs have been synthesized, which are created from the chemical bond (direct or indirect by means of a spacer consisting of amino acids or peptides with a short amino acid chain) or simple association of some antineoplastic drugs containing a lactonic ring (such as, for example, doxorubicin, paclitaxel, vincristine, vinblastine and derivates of camptothecins) with hyaluronic acid (HA) (U.S. Pat. No. 6,291,671).

Other conjugates comprise antineoplastic drugs such as paclitaxel and camptothecins bound to a polymer consisting of polyglutamic acid possibly associated with HA (U.S. Pat. No. 5,977,163).

Other new types of chemotherapy drugs are also known, represented by antitumoral doxorubicin covalently bound both to HA (chemically modified with dihydrazide) and to a carrier such as the polymer hydroxy-propyl-methacrylamide (international patent application WO 02/090390).

New carrier drugs are also known, consisting of polysaccharides chemically conjugated to amino acid chains in turn covalently bound to antineoplastic drugs such as doxorubicin (U.S. Pat. No. 5,688,931). Furthermore, for the same reason, other release systems have been perfected, consisting, for example, in the encapsulation of doxorubicin in liposomes containing lipidic derivatives of HA (Peer D. et al., Neoplasia, 2004, 6(4):343-353; Eliaz R. E. et al., Cancer Research, 2001, 61:2592-2601).

It is known, for example, that to overcome the problems of camptothecins derivatives, to alternate their pharmacokinetic profile and reduce their toxicity increasing their therapeutic efficacy, irinotecan has been conjugated with the polymer/carrier carboxy-methyl-dextran by means of a spacer represented by a triglycine peptide (Satoshi Okuno et al., Cancer Research, 2000, 60:2988-2995; U.S. Pat. No. 5,892,043).

The resulting prodrug has proved to be active in its therapeutic efficacy as it remains in circulation for a prolonged period of time increasing its accumulation in the tumoral mass, contemporaneously reducing its systemic toxicity; for many of the conjugates previously described, however, definite experimental data are not yet available, which document its efficacy with respect to the non-conjugated drug.

The derivative of paclitaxel is also known, covalently bound to HA previously derivatised with hydrazide (U.S. Pat. No. 5,874,417), or bound directly to HA, or indirectly by means of a spacer of a varying nature capable of forming different types of chemical bonds which increase the solubility and consequently the efficacy of the drug (patent application EP 1560854).

The present invention describes and claims new conjugates of HA obtained from the indirect bond between the polysaccharide and liposoluble antineoplastic drugs such as, for example, irinotecan and Vinca alkaloids, or with soluble or partially soluble chemotherapy drugs such as doxorubicin and analogous products of pyrimidine, to overcome problems linked to their solubility (if present), their toxicity and, above all, to re-establish and increase the therapeutic efficacy of the drug in tumoral cells which have acquired pharmacological resistance to the drug itself. The state of the art represented by the derivatives previously described is consequently surpassed herein as the Applicant is capable of demonstrating the pharmacological superiority of the new conjugates, object of the present invention, thanks to the extremely high cytotoxic capacity of these derivatives towards neoplastic cells.

This new pharmacological efficacy allows the application in clinical pharmacology of innovative chemotherapic therapies, for the treatment of primary and/or secondary tumors which no longer respond to any medical treatment following the formation of Multi Drug Resistance (MDR) which generally jeopardizes the possibility of an effective treatment of the patient and consequently, in last analysis, drastically reduces his life expectancy.

By solving/overcoming MDR, the new derivatives, object of the present invention, change the final prognosis of the patient, consequently allowing the solution/reduction of the tumoral pathology.

DETAILED DESCRIPTION OF THE INVENTION

The present invention describes and claims a new group of conjugates/derivatives and their preparation process, consisting of hyaluronic acid (HA) (and/or its derivatives) and antitumoral drugs, indirectly conjugated by means of a molecular bridge called "spacer" consisting of an aliphatic, araliphatic, alicyclic, or heterocyclic chain, linear or branched with or without heteroatoms.

In particular, they are object of the present invention chemical-pharmaceutical conjugates of hyaluronic acid and/ or its derivatives obtained through an indirect binding between the polysaccharide and a drug with an antitumoral action, via a molecular spacer which forms an ester or amide bond with the carboxylic group of HA and/or its derivative, with the proviso that said spacer is not a hydrazide or a polypeptide.

The HA (and/or one of its derivatives) and the drug are therefore indirectly conjugated by means of one or more covalent bonds of the ester or amide type which partially or totally involve the carboxylic groups of the polysaccharide and a chemical function (for example a hydroxyl, a carboxyl, an amine group, etc.) belonging to the spacer which in turn is bound to the antitumoral drug selected, as described in detail hereunder.

The derivatives which can be obtained according to the present invention have different physico-chemical properties which can be modulated through the selection of the type of bond and substitution degree, so as to improve the characteristics of the starting chemotherapy drug, such as:

solubility, mechanical and rheological characteristics, resistance to hydrolytic degradation, making the new conjugate more efficient in its cytotoxic action, a derivative which will have a new action mechanism thus overcoming pharmacological resistance to the drug itself acquired by the tumoral cell (as described above).

As is known, many antitumoral chemotherapy drugs have a limited, if not non-existent, solubility in water or saline solutions; this means that for their administration, resort must be made to organic solvents and oils which, although bringing the drug into solution, have an intrinsic toxicity with side-effects which require medication interventions prior to the administration of the product.

In some cases, for the chemotherapy drug Irinotecan, the active form (SN38) is even chemically modified (prodrug) to make it soluble and to promote the release of its metabolite which is active after intravenous administration. This however causes a low availability of the metabolite SN38 in the target site therefore requiring the administration of high cytotoxic dosages with a consequent amplification of undesired side effects.

innotecan

SN-38

International literature (Mathijssen R H et al., Clin Cancer Res, 2001, 7:2182-2194) indicates that the antitumoral activity of SN38 is from 100 to 1000 times higher with respect to its commercial prodrug; consequently the possibility of conjugating SN38 with hyaluronic acid or one of its derivatives according to the present invention, allows compounds with an increased efficacy to be obtained and, thanks to the necessity of lower administration dosages, with lesser side-effects linked to the dispersion of the drug in areas not struck by neoplasia. The conjugation of antitumoral chemotherapy drugs with HA also allows the active principle to be "directed" towards its target, and consequently towards the neoplastic tissue. Emphasis is therefore given to an active targeting mechanism between conjugate and neoplastic cell which increases the local concentration of drug close to the neoplastic area and consequently the efficacy. In this way, moreover, by reducing the distribution of the derivative to the healthy tissues, a greater tolerability of the product is guaranteed with respect to the free drug.

A second fundamental advantage deriving from the present invention is the possibility, mainly thanks to the presence of chemically modified HA, of technologically transforming the conjugate into a three-dimensional biomaterial (to be applied locally) processed in various forms such as, for example, hydrogel, nano- or microspheres or of fibres in turn spun as woven or non-woven products; in this case the chemically modified polysaccharide matrix is in close contact with the tumoral mass, acts as a controlled release system of the drug in the application site and therefore favours a greater efficacy on the part of the drug itself. Once the antineoplastic action has been exerted, the derivative degrades naturally and safely for the organism, completely freeing the antitumoral active principle and hyaluronic acid. The products generated by the invention, whether they be in the form of classical pharmaceutical compositions or degradable biomaterials, are therefore characterized by a greater tolerability with respect to the non-modified active principle and a higher pharmacological activity, in some cases even by several orders of magnitude with respect to that expressed by the active principle forming them; both effects can be attributed to the specific affinity of hyaluronic acid towards receptors such as CD44 present in tumoral cells. These effects are highlighted when the conjugated drug is administered in the form of a three-dimensional material, in direct contact with the neoplasia. The combination of these characteristics is such that the derivatives/conjugates of the present invention distinctly surpass what is available in the state of the art in the local or systemic therapy of various kinds of neoplasia and of different origins, which have also become resistant to traditional chemotherapic therapy.

The hyaluronic acid used in the present invention has a molecular weight varying from 400 to 3,000,000 Da, preferably ranging from 5,000 to 1,000,000 Da, and even more preferably from 30,000 to 500,000 Da, it can be of an extractive, fermentative or biosynthetic origin. The covalent bond with the spacer involves the carboxylic group of D-glucuronic acid of the repetitive unit of the polymer, in a percentage varying from 1 to 100% (substitution degree), which forms an ester or amide bond with the functional group of the molecular spacer selected which consequently acts as a connection the between hyaluronic acid and chemotherapic drug.

The spacer agent consists of an aliphatic, araliphatic, alicyclic, or heterocyclic chain, linear or branched containing or not containing heteroatoms, which can comprise hydroxyl, carboxyl, carbonyl, amine groups (with the exclusion of hydrazides and polypeptides), epoxy groups, chlorides of acids, thiols, nitriles, halogens, anhydrides, isocyanates, and isothiocyanates; bromides, iodides and chlorides of carboxylic acids with a $C_2$ to $C_{10}$ aliphatic chain are preferred, and in particular bromides such as bromopropionic acid or bromobutyric acid. The substitution degree preferably ranges from 1 to 50% and even more preferably from 1 to 20%; for conjugation with doxorubicin a substitution from 3 to 15% is preferable whereas for conjugation with SN38 a substitution from 1 to 10% is preferred.

The derivatives of HA which can be used in the new conjugates, object of the present invention, are listed below:
1. HA salified with organic and/or inorganic bases having a molecular weight of 50-730 KDa (EP0138572 B1) or a high molecular weight 750-1230 KDa, (EP 535200 B1);
2. Hyaff®: esters of HA with alcohols of the aliphatic, araliphatic, cyclo-aliphatic, aromatic, cyclic and heterocyclic series, with an esterification percentage which can vary depending on the type and length of alcohol used, from 1 to 75%, preferably from 30 to 50% (EP 216453 B1);
3. Hyadd™: amides of HA with amines of the aliphatic, araliphatic, cyclo-aliphatic, aromatic, cyclic and heterocyclic series, with an amidation percentage ranging from 1 to 10%, preferably 4% (EP 1095064 B1);
4. O-sulfated derivatives of HA up to the $4^{th}$ sulfation degree (EP 0702699 B1);
5. ACP®: internal esters of HA with an internal esterification percentage ranging from 0.5 to 10% and preferably 5% (EP 0341745 B1);
6. Deacetylates of HA: derive from the deacetylation of the N-acetyl-glucosamine fraction with a deacetylation percentage preferably ranging from 0.1 to 30%, whereas all the carboxyl groups of HA can be salified with organic and/or inorganic bases (EP 1313772 B1);
7. Hyoxx™: percarboxylated derivatives of HA obtained from the oxidation of the primary hydroxyl of the N-acetyl-glucosamine fraction with a percarboxylation degree ranging from 0.1 to 100%, preferably from 25 to 75%. All the carboxylic groups of HA can be salified with organic and/or inorganic bases (patent application EP 1339753).

The drugs used in the conjugation reaction with HA preferably belong to the following categories:
nitrosureas,
antimetabolites: such as, for example, analogous products of folic acid (among which methotrexate), analogous products of pyrimidine (among which fluorouracyl and 1-β-D-Arabino-furanosylcytosine: Ara-C),
alkaloids: such as, for example, vincristin and vinblastin (Vinca alkaloids) and the active metabolite of irinotecan, SN38,
antibiotics and analogous products: such as, for example, doxorubicin and epirubicin,
biological response modifiers,
diterpenoids,
synthetic hormones and antihormones: such as, for example, extradiol.

Doxorubicin and the irinotecan metabolite, SN38, are particularly suitable for the purposes of the present invention.

The drugs identified and hyaluronic acid (and/or one of its derivatives) are bound indirectly by means of a spacer through the formation of ester bonds with the following procedures:

1. a functional group of the suitably selected spacer (such as for example, a carboxyl group, an amine group, a halide, etc.), also containing a second group (called "leaving group") capable of reacting with the carboxyl function of HA (for example, a halide: bromine, iodine or chlorine) reacts with a functional group belonging to the antitumoral molecule represented, for example, by a hydroxyl, an amine, a carboxyl or a mercaptan. The reaction may possibly require the activation of one of the functions involved by means of an activating agent (for example the activation of a carboxyl group by means of carbodiimides). In a second phase, by direct contact with a tetraalkylammonium salt (preferably tetrabutylammonium) of HA in an anhydrous environment, the compound consisting of the modified drug reacts giving rise to a nucleophilic substitution of the outgoing group (for example bromide) at the carboxyl of the HA, causing the formation of an ester bond between HA and spacer;
2. the carboxyl group of hyaluronic acid or one of its derivatives is bound by nucleophilic attachment to a suitable spacer which is subsequently bound to a function of the antitumoral molecule (in all ways known to experts in the field);
3. the carboxyl group of HA or one of its derivatives is activated with an activating agent, for example a carbodiimide, and is reacted with a hydroxyl function of the suitably selected spacer, previously or subsequently bound to the drug (in all ways known to experts in the field).

The drugs identified and hyaluronic acid (and/or one of its derivatives) are bound indirectly by means of a spacer through the formation of amide bonds with the following procedures:

1. the carboxyl group of hyaluronic acid or one of its derivatives is activated with an activating agent such as, for example, a carbodiimide, and reacted with an amine function of the suitably selected spacer, previously or subsequently bound to the drug selected (in all ways known to experts in the field).

Oncological applications relating to the use of conjugates consisting of hyaluronic acid (and/or one of its derivatives) and antitumoral active principle are closely linked to the response of the neoplasia to the conjugated drug. In accordance with the uses envisaged, the bioconjugates can therefore be administered orally, intravenously, intra-arterially, intrathecally, intramuscularly, subcutaneously, intraperitoneally, intra-articularly, topically, transdermally, loco-regionally, or in a combination thereof (both a local and systemic administration procedure is therefore claimed). The neoplasias involved in the treatment can for example be (without limits) tumors of the pancreas, breast, colon-rectum, lung and respiratory system in toto, head-neck, liver, stomach, testicles, ovary, endometrium, prostate, bladder, brain, leukemia, lymphomas, melanoma, Kaposi's sarcoma, osteosarcoma, neuroblastoma and skin cancer.

Some preparation examples of bioconjugates between hyaluronic acid and/or its derivatives and chemotherapy drugs with an antitumoral activity are provided hereunder for purely illustrative and non-limiting purposes.

Example 1

Figure 1:
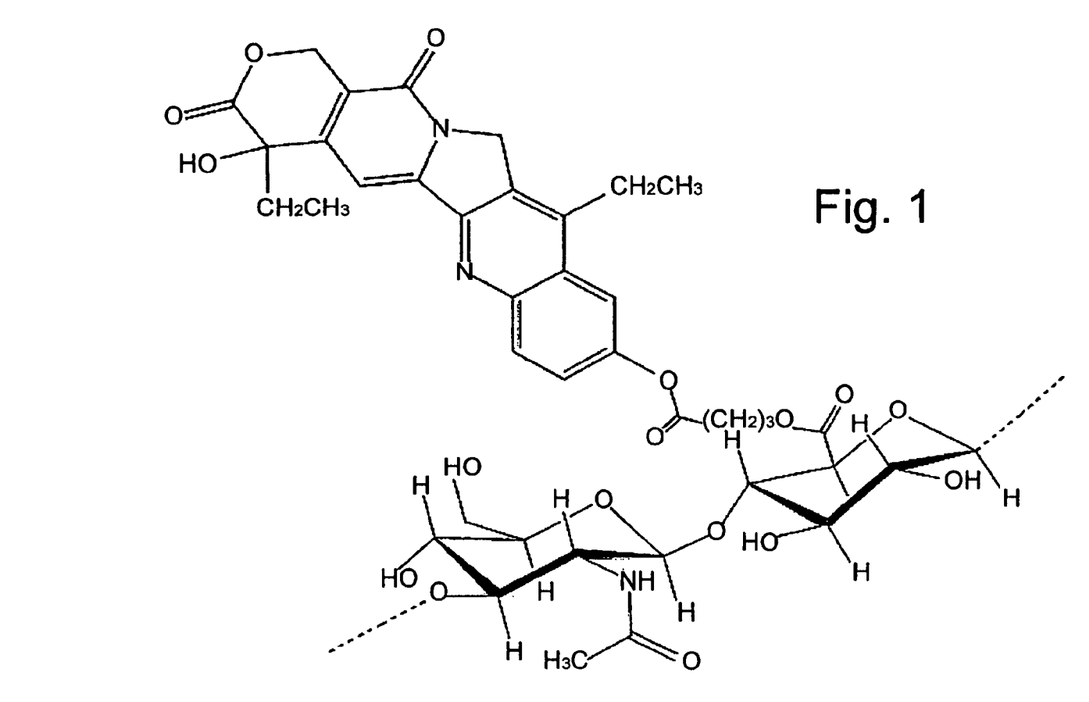
FIG. 1 sets forth the structural formula of the ester derivative hyaluronic acid described in Example 1.

Preparation of an Ester Derivative of Hyaluronic Acid Having a MW of 200 kDa and SN-38 with a Substitution Degree of about 15% (FIG. 1)

199 mg of SN-38 are dissolved in 50 ml of Acetonitrile and 383 mg of 1-(3-dimethylaminopropyl)-3-ethylcarbodiimmide (EDC), 258 mg of 4-bromobutyric acid and 40 mg of DMAP are added to the solution. The development of the solution is followed by means of TLC chromatography (silica stationary phase with fluorescence indicator and chloroform-acetonitrile eluent 60:40). The product is recovered by means of precipitation and purified by chromatography on a silica column using chloroform:methanol 99:1 as eluent. The intermediate thus obtained is dried at room temperature under high vacuum. 0.84 g of hyaluronic acid tetrabutylammonium salt (HATBA) are dissolved in 43 ml of N-methyl-2-pyrrolidone (NMP) at room temperature. The intermediate is added to the solution and the whole mixture is left to react at room temperature. After 7 days of reaction the solution is diluted with 5 ml of water and 5 ml of saturated sodium chloride. The whole mixture is left under stirring for 1 hour to allow the exchange of the sodium with the TBA ion. Ethanol is subsequently added dropwise and the filamentous product obtained is dissolved in water, dialyzed and, at the end, lyophilized.

Example 2

Preparation of an Ester Derivative of Hyaluronic Acid (MW 31 kDa) and SN-38 with a Substitution Degree at the Carboxyl of about 10%

200 mg of SN-38 are dissolved in 50 ml of DMSO and 1.00 g of ethylene carbonate are added to the solution. The solution is heated to 50° C. and the development of the solution is followed by means of TLC chromatography on silica plates. At the end of the reaction, the product is recovered by means of precipitation and dried at room temperature under a high vacuum. 175 mg of intermediate thus obtained are dissolved in an anhydrous mixture of DMSO/pyridine 90:10 with 85 mg of p-toluenesulfonyl chloride. When the intermediate has been converted into the corresponding toxylate, it is recovered by precipitation and dissolved in a solution of HATBA in NMP (0.68 g of polymer in 34 ml of NMP). The whole mixture is left to react for 7 days at room temperature. 4 ml of a saturated solution of NaCl is added to the solution and the mixture is left under stirring for 1 hour to allow the exchange of the sodium with the TBA ion. Ethanol is subsequently added dropwise and the filamentous product obtained is dissolved in water, dialyzed and, at the end, lyophilized.

Example 3

Preparation of an Ester Derivative of Hyaluronic Acid with a MW of 55 kDa with Vinblastine with a Substitution Degree at the Carboxyl of about 10%

308 mg of vinblastine are dissolved in 30 ml of chloroform and 120 mg of 4-bromobutyric acid and 150 mg of EDC are then added. After a while, water is added to the solution for the elimination of the bromide and carbodiimide. The organic solution is anhydrified by means of sodium sulfate and the solvent is eliminated on a rotavapour. 300 mg of intermediate thus obtained are added to 1.70 g of HATBA dissolved in an anhydrous NMP and the solution is kept under stirring at room temperature for seven days. At the end, the whole mixture is left under stirring for 1 hour with 6 ml of saturated solution of NaCl to allow the exchange of the sodium with the TBA ion. Ethanol is subsequently added dropwise and the filamentous product obtained is dissolved in water, dialyzed and, at the end, lyophilized.

Example 4

Preparation of an Ester Derivative of Hyaluronic Acid with a MW of 440 kDa and 5-Fluorouracyl with a Substitution Degree at the Carboxyl of about 15%

680 mg of ethylene carbonate and about 10 mg of NaOH are added to 510 mg of fluorouracyl dissolved in 15 ml of DMF. The whole mixture is heated and the reaction is left to continue for 1 hour at reflux temperature. The product recovered by precipitation is dissolved in an anhydrous mixture of DMSO/pyridine 50/50 with 1.00 g of p-toluenesulfonyl chloride. After about 15 hours, the product is recovered by precipitation and added to a solution of HATBA dissolved in DMSO (3.60 g in 180 ml of DMSO). The solution is kept under stirring at 38° C. for about 3 days and at the end 20 ml of water milliQ and 7 ml of a saturated solution of NaCl are added. The whole mixture is left under stirring for 1 hour to allow the exchange of the sodium with the TBA ion. Ethanol is subsequently added dropwise and the filamentous product obtained is dissolved in water, dialyzed and lyophilized.

Example 5

Preparation of an Ester Derivative of Hyaluronic Acid with a MW of 200 kDa and 1-β-D-Arabino-furanosylcytosine (Ara-C) with a Substitution Degree at the Carboxyl of about 18%

100 mg of Ara-C, 80 mg of EDC and 69 mg of 4-bromobutyric acid are dissolved in 10 ml of water. The whole mixture is reacted for about 1 hour and at the end the solvent is eliminated by evaporation at reduced pressure on a rotavapour. The product is purified by means of column chromatographic separation. The intermediate thus obtained is dissolved in a solution at 20 mg/ml of 1.10 g of HATBA in DMSO and reacted for 7 days at room temperature. 5 ml of a saturated solution of NaCl are added in order to recover the product, thus allowing salification with sodium of the carboxyls of hyaluronic acid. The polymer is precipitated by adding ethanol dropwise, and after filtering it and redissolving it in water, it is dialyzed to eliminate the residues of solvent and salt and finally lyophilized.

Example 6

Preparation of an Ester Derivative of Hyaluronic Acid with a MW of 120 kDa and 17β-Extradiol with a Substitution Degree at the Carboxyl of about 20%

140 mg of 17β-extradiol are dissolved in 50 ml of DMSO and 380 mg of 1-(3-dimethylaminopropyl)-3-ethylcarbodiimide (EDC), 262 mg of 4-bromobutyric acid are added to the solution. The product is recovered by precipitation and purified by chromatography on a silica column. The intermediate thus obtained is dried at room temperature under a high vacuum. 0.80 g of hyaluronic acid tetrabutylammonium salt (HATBA) are dissolved in 40 ml of N-methyl-2-pyrrolidone (NMP) at room temperature. The intermediate is added to the solution and the whole mixture is left to react at room temperature. After 7 days of reaction the solution is diluted with 5 ml of water and 5 ml of a saturated solution of sodium chloride. The whole mixture is left under stirring for 1 hour to allow the exchange of the sodium with the TBA ion. Ethanol is then added dropwise and the filamentous product obtained is dissolved in water, dialyzed and, at the end, lyophilized.

Example 7

Preparation of the Partial Ester Between Hyaluronic Acid 200 kDa and SN38 and Auto-Crosslinking of HA Derivative 200 mg of SN38 are dissolved in 50 ml of DMSO and 375 mg of 1-(3-dimethylaminpropyl)-3-ethylcarbodiimide (EDC), 330 mg of 4-bromobutyric acid are added to the solution. The development of the solution is monitored by means of TLC chromatography (silica stationary phase with fluorescence indicator and chloroform-acetonitrile 60:40 eluent). The product is recovered by means of precipitation and purified by chromatography on a silica column using chloroform:methanol 99:1 as eluent. The intermediate thus obtained is dried at room temperature under high vacuum. 0.84 g of hyaluronic acid tetrabutylammonium salt (HATBA) are dissolved in 43 ml of N-methyl-2-pyrrolidone (NMP) at room temperature. After leaving the solution to react for 7 days, 34 mg of triethylamine are added to the reaction solution and the whole mixture is stirred for 30'.

A solution of 87 mg of 2-chloro-1-methyl-pyridine iodide in 10 ml of DMSO is slowly added dropwise over a period of 45' and the mixture is maintained at 30° for 15 h.

A solution consisting of 15 ml of water and 0.5 g of sodium chloride is then added and the resulting mixture is slowly poured into 300 ml of acetone under continuous stirring. A precipitate is formed which is filtered and washed three times with 25 ml of acetone-water 5:1 and three times with acetone (50 ml). The product is dried under a high vacuum at 38° C.

Example 8

Figure 2:
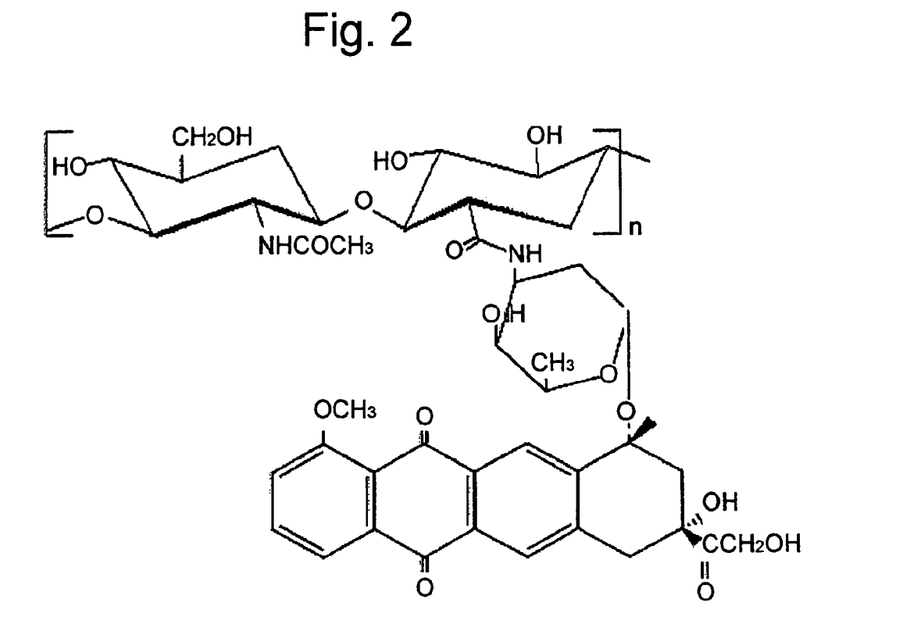
FIG. 2 sets forth the molecular structure of the amide derivative hyaluronic acid with doxorubicin described in Example 8.

Preparation of an Amide Derivative of Hyaluronic Acid 220 kDa with Doxorubicin with a Substitution Degree at the Carboxyl of about 5% (FIG. 2)

2.00 g of HATBA are dissolved in 100 ml of DMSO with a low water content. The solution is insufflated with gaseous hydrochloric acid until, upon removing an aliquot of the solution and diluting it with water 1:10, the pH proves to be between 4.5 and 5. Carbonyldiimidazole (55 mg) is subsequently added to the solution and the whole mixture is left under stirring at room temperature for 1 h. At the end, 1.4 g of doxorubicin are added to the solution and the mixture is left to react for 24 hours at room temperature. 5 ml of a saturated solution of NaCl are added to recover the product, thus allowing salification with sodium of the carboxyls of hyaluronic acid. The polymer is precipitated by adding ethanol dropwise and, and after filtering it and redissolving it in water, it is dialyzed to eliminate the residues of solvent and salt and finally lyophilized.

Example 9

Preparation of the Partial Ester Between Hyaluronic Acid and Doxorubicin and Auto-Crosslinking with Ugi Condensation 500 mg of polymer obtained according to example 8 are dissolved in 5 ml of distilled water. The pH of the solution is lowered to about 4 by the addition of concentrated hydrochloric acid. 15 mg of lysine ethyl ester dihydrochloride, 250 µl of aqueous solution of formaldehyde at 40% and 250 µl of cyclohexylisocyanide are added to the solution. After 15' of reaction the gel is put in dialysis in a basic solution of sodium carbonate for about 24 h and at the end is dialyzed against water until a conductivity of the solution of less than 40 µs. The polymer is recovered by lyophilization.

Example 10

Preparation of an Ester Derivative of Hyaluronic Acid with a MW of 200 kDa and Doxorubicin with a Substitution Degree at the Carboxyl of about 10%

325 mg of Doxorubicin Hydrochloride are dissolved in 50 ml of NMP, after adding 0.3 ml of Et$_3$N, 420 mg of 1-(3-dimethylaminopropyl)-3-ethylcarbodiimmide (EDC) and 280 mg of 4-bromobutyric acid are subsequently added to the solution. The development of the solution is monitored by means of TLC chromatography (silica stationary phase with fluorescence indicator and dichloromethane-methanol eluent 80:20). The product is purified by chromatography on a column using chloroform:methanol 99:1 as eluent.

The intermediate thus obtained is dried at room temperature under high vacuum. 0.75 g of hyaluronic acid tetrabutylammonium salt (HATBA) are dissolved in 40 ml of N-methyl-2-pyrrolidone (NMP) at room temperature. The intermediate is added to the solution and the whole mixture is left to react at room temperature. After 7 days of reaction the solution is diluted with 5 ml of water and 5 ml of saturated sodium chloride. The whole mixture is left under stirring for 1 hour to allow the exchange of the sodium with the TBA ion. Ethanol is subsequently added dropwise and the filamentous product obtained is dissolved in water, dialyzed and, at the end, lyophilized.

In Vitro Experimentation:
Evaluation of the Antiproliferative Activity of the Ester Conjugate HA/SN38 having a Substitution Degree Equal to 10% and 15%, on the Cellular Line of Colic Adenocarcinoma HT29

Aliquots of the derivatives obtained from examples 1 and 2 are characterized by means of a cytotoxicity test in vitro on a line of colic tumoral cells called HT29. The comparison was effected with SN38 dissolved in DMSO. The HA derivatives are solubilized in a glucosated solution at 5% at a concentration of 5 mg/ml. The test is effected by depositing on a plate with 96 cavities, 3000 cells per cavity; after 24 hours of incubation at 37° C., the cells are put in contact with the solutions and after a further 48 hours the cell vitality is determined by means of a MTT colorimetric assay (Dezinot F. et al., J. Immunol Methods, 1986, 22(89):271-277).

Figure 4:
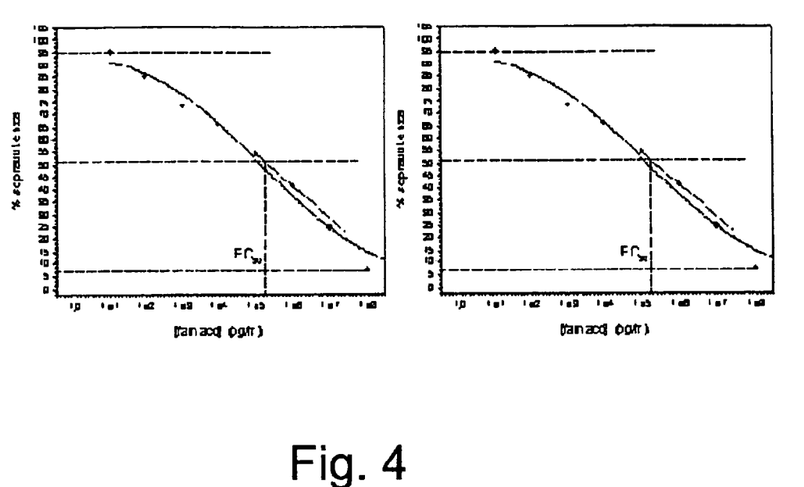
FIG. 4 shows graphs of proliferation curves referring to two ester conjugates of hyaluronic acid.

The proliferation curves referring to the two ester conjugates of HA are shown in the graphs (on the left the cytotoxic activity of the derivative at 15%, on the right that at 10%), see FIG. 4.

By comparing the data of EC$_{50}$ with SN38 in dimethylsulfoxide (DMSO) the following results are obtained:

| Compound | EC$_{50}$ (nM) |
| --- | --- |
| HA-SN38 15% | 5.2 |
| HA-SN38 10% | 8.5 |
| SN38 in DMSO | 5.0 |

The in vitro results confirm that the new HA/SN38 derivatives show the same cytotoxic activity of the active metabolite SN38 which, as described above, has from 100 to 1,000 times the activity of its commercial prodrug, Irinotecan. The experimentation effected therefore affirms a much higher efficacy of the new derivative with respect to the reference drug currently used in clinical practice.

In order to demonstrate what is stated above with respect to the efficacy of the new conjugates (object of the present invention) as antineoplastic drugs capable of overcoming the pharmacological resistance acquired by neoplastic cells no longer sensitive to the drug itself, the following in vitro experimentations were effected:
Cytotoxicity Test in DHD/K12 Cells of the Chemotherapy Drug Doxorubicin Compared with its Amide Conjugate with HA The cellular line used derives from rats of the BDIX strain treated with 1,2-dimethylhydrazine. These cells in fact express the same tumoral antigens as the human colon-rectum adenocarcinoma and, for this reason, they are used as a preclinical study model in vitro for the same type of tumor.

The above cellular line has also acquired resistance to chemotherapy treatment (this is called "Multi Drug Resistance": MDR).

In order to evaluate the degree of cellular vitality the LIVE/DEAD Cell Vitality Assay (Molecular Probes) was used, which allows metabolically active cells to be distinguished from dead cells: the latter emit green fluorescence at a nuclear level whereas live cells emit red fluorescence localized on the cellular membrane and in the cytoplasm. After colouring, the cells were analyzed using a confocal microscope and the percentage of live/dead cells was evaluated by counting a minimum of 500 live or dead cells per sample.

Figure 3:
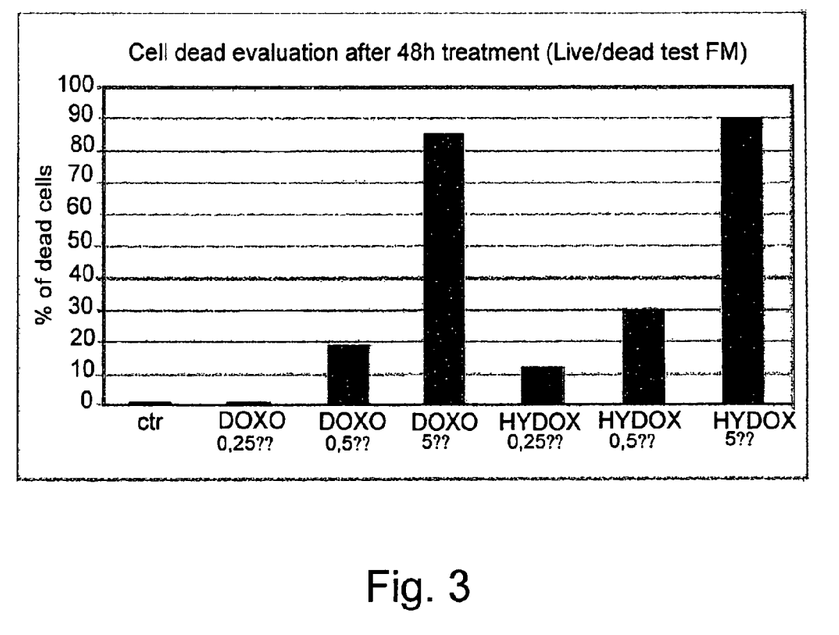
FIG. 3 tabulates the results of tests evaluating the antiproliferative activity of two conjugates.

The amide conjugate of doxorubicin with HA (Hydox) was used for the experimentation, having a substitution degree of 5% obtained according to example 8, compared with the drug as such, at different concentrations. FIG. 3: after 48 hours of treatment, the results of the LIVE/DEAD test graphed in FIG. 3, clearly indicate how the Hydox conjugate is capable of exerting, in a dose-dependent way, a cytotoxic effect in cells which have acquired a certain resistance to chemotherapy, much higher than the corresponding non-conjugated doxorubicin, used under the same concentrations. Hydox, in fact, also proves to be active at low concentrations such as 0.25 μM, whereas the reference drug at this dosage does not have any cytotoxic effect. On doubling the concentration, the conjugate in question has 35% more cytotoxicity, therefore allowing the use of lower dosages of drug with lesser side-effects in cells which no longer respond to classical chemotherapic therapies due to acquired resistance to the above antineoplastic drugs.

The description of the invention being as such, it is evident that these methods can be modified in various ways. Said modifications should not be considered as diverging from the spirit and perspectives of the invention and all modifications which appear evident to experts in the field are included in the scope of the following claims.

The invention claimed is:

1. A conjugate of hyaluronic acid or a derivative thereof with SN-38, wherein a molecular spacer is bonded to said hyaluronic acid or a derivative thereof via an ester or amide bond between said molecular spacer and a carboxylic group of said hyaluronic acid or a derivative thereof and said SN-38 is bonded to said molecular spacer, said conjugates being able to treat alkaloid drug resistant cancer cells;
   wherein the substitution degree of the carboxyl of hyaluronic acid by the spacer bound to SN38 ranges from 3 to 15%; and
   wherein said molecular spacer is a member selected from the group consisting of bromides, iodides, and chlorides of carboxylic acids with a $C_2$ to $C_{10}$ acid or aliphatic chain.

2. A conjugate of hyaluronic acid or a derivative thereof with SN-38, wherein a molecular spacer is bonded to said hyaluronic acid or a derivative thereof via an ester or amide bond between said molecular spacer and a carboxylic group of said hyaluronic acid or a derivative thereof and said SN-38 is bonded to said molecular spacer, said conjugates being able to treat multidrug resistant cancer cells;
   wherein the substitution degree of the carboxyl of hyaluronic acid by the spacer bound to SN38 ranges from 3 to 15%; and
   wherein said molecular spacer is a member selected from the group consisting of bromides, iodides, and chlorides of carboxylic acids with a $C_2$ to $C_{10}$ acid or aliphatic chain.

3. The conjugate according to claim 2, wherein said molecular spacer is bromopropionic acid or bromobutyric acid.

4. The conjugate according to claim 2, wherein said molecular spacer is bromobutyric acid.

5. The conjugate according to claim 2, wherein the hyaluronic acid and/or one of its derivatives has a molecular weight ranging from 400 to $3 \times 10^6$ Da.

6. The conjugate according to claim 5, wherein the hyaluronic acid has a molecular weight ranging from 5,000 to $1 \times 10^6$ Da.

7. The conjugate according to claim 6, wherein the hyaluronic acid has a molecular weight ranging from 30,000 to $0.5 \times 10^6$ Da.

8. The conjugate according to claim 2, wherein the derivative of hyaluronic acid is a salt with organic and/or inorganic bases.

9. A pharmaceutical composition comprising one or more of the conjugates according to claim 2, as active principle.

10. The pharmaceutical composition according to claim 9 for oral, intravenous, intra-arterial, intra-articular, subcutaneous, intrathecal, intraperitoneal, transdermal intramuscular, or topical administration.

11. A three dimensional biomaterial, comprising the conjugate according to claim 2 processed in the form of hydrogels, nano- and microspheres, woven, or nonwoven spun fibres.

12. A method for the treatment for a tumor in a patient which comprises administering to a patient in need thereof an effective antitumor amount of a conjugate according to claim 2.

13. The method according to claim 12 wherein said tumor is a type selected from a group consisting of tumors of the pancreas, breast, colon-rectum, lung and respiratory system in toto, head-neck, liver, stomach, testicles, ovary, endometrium, prostate, 20 bladder, brain, leukemia, lymphomas, melanoma, Kaposi's sarcoma, osteosarcoma, neuroblastoma and skin cancer.

14. A method for treating multidrug resistant cancer cells in a patient, comprising:
   administering to a patient in need thereof an effective amount of a conjugate of hyaluronic acid or a derivative thereof with SN-38,
   wherein a molecular spacer is bonded to said hyaluronic acid or a derivative thereof via an ester or amide bond between said molecular spacer and a carboxylic group of said hyaluronic acid or a derivative thereof and said SN-38 is bonded to said molecular spacer;
   wherein the substitution degree of the carboxyl of hyaluronic acid by the spacer bound to SN38 ranges from 3 to 15%; and
   wherein said molecular spacer is a member selected from the group consisting of bromides, iodides, and chlorides of carboxylic acids with a $C_2$ to $C_{10}$ acid or aliphatic chain.

* * * * *